United States Patent [19]

Maki et al.

[11] 4,319,054

[45] Mar. 9, 1982

[54] PROCESS FOR PRODUCING PYROGALLOL

[75] Inventors: Takao Maki, Fujisawa; Kenji Murayama, Yokohama, both of Japan

[73] Assignee: Mitsubishi Chemical Industries Limited, Tokyo, Japan

[21] Appl. No.: 213,900

[22] Filed: Dec. 8, 1980

[30] Foreign Application Priority Data

Dec. 12, 1979 [JP] Japan .............................. 54/161097
May 19, 1980 [JP] Japan .............................. 55/66073
Jun. 17, 1980 [JP] Japan .............................. 55/81946

[51] Int. Cl.³ .......................................... C07C 37/06
[52] U.S. Cl. .................... 568/772; 568/740; 568/763; 568/799
[58] Field of Search .............. 568/772, 799, 740, 763

[56] References Cited

U.S. PATENT DOCUMENTS 3,780,114 12/1973 Dewaele ............................ 568/772
4,046,817 9/1977 Shipchandler ..................... 568/763
4,160,113 7/1979 Muller et al. ...................... 568/772
4,254,288 3/1981 Gladwin ............................ 568/740

FOREIGN PATENT DOCUMENTS 51-91215 10/1976 Japan ................................. 568/772

OTHER PUBLICATIONS

Doklady Akademii Nau., USSR, pp. 1354–1355, 198 (1971).
Doklady Akademii Nauk., pp. 145–147, 185 (1969).

*Primary Examiner*—Werren B. Lone
*Attorney, Agent, or Firm*—Bierman & Bierman

[57] ABSTRACT

There is disclosed a process for producing pyrogallol by dehydrogenation of cyclohexane-1,2,3-triol in the presence of a platinum group metal catalyst in an inert gas stream. The catalyst contains, as modifier, (a) at least one alkali metal salt and/or (b) at least one member selected from the group consisting of gold, tellurium, silver, arsenic, selenium, indium, antimony, bismuth, copper and zinc, with the Pd-Te catalyst being preferred. The catalyst ingredients are supported on a carrier. The process gives high selectivity of pyrogallol.

20 Claims, No Drawings

PROCESS FOR PRODUCING PYROGALLOL

FIELD OF THE INVENTION

This invention relates to a process for producing pyrogallol comprising subjecting cyclohexane-1,2,3-triol to dehydrogenation.

BACKGROUND OF THE INVENTION

Pyrogallol is a useful compound suitable for use as photographic and dyeing industries or an intermediate in synthesis of organic chemicals. It is now being produced by thermal decarboxylation of gallic acid which is obtained from naturally occurring materials, and thus pyrogallol is expensive and its supply and application are limited. In view of the above, in order to obtain pyrogallol on a large scale at a low cost, the synthesis of pyrogallol from a cheap chemical compounds has been desired.

Production of phenols by dehydrogenation of a cyclohexanols has already been known. For example, "Doklady Akademii Nauk. SSSR. 185, 145 (1969)" teaches production of catechol by dehydrogenation of cyclohexane-1,2-diol and "Doklady Akademii Nauk. SSSR, 198, 1354 (1971)" discloses production of pyrogallol by dehydrogenation of cyclohexane-1,2,3-triol. Both processes employ a gas phase dehydrogenation reaction in which starting material is contacted with a catalyst system comprising metallic palladium and potassium carbonate supported on activated carbon at 300° C. in a hydrogen stream.

We have examined the procedures disclosed in the literature above and found that cyclohexane-1,2-diol can successfully be produced but dehydrogenation of cyclohexane-1,2,3-triol results in mainly catechol and the selectivity of pyrogallol is very low. In order to improve the selectivity of pyrogallol in such dehydrogenation, we have conducted intensive studies and have found that if the reaction is carried out in a stream of an inert gas such as nitrogen, the selectivity of pyrogallol can be increased. This invention is conceived on the basis of this knowledge.

SUMMARY OF THE INVENTION

An object of this invention is to provide a process for producing pyrogallol comprising subjecting cyclohexane-1,2,3-triol to dehydrogenation in the presence of a catalyst system containing a platinum group metal in an inert gas stream.

Another object of this invention is to increase the selectivity of pyrogallol by the use of a novel catalyst system.

DETAILED DESCRIPTION OF THE INVENTION

Cyclohexane-1,2,3-triol which is the starting material of the process according to this invention can be produced by any of the known processes, for example, by hydration of 1,2-epoxycyclohexan-3-ol which can be obtained by oxidation of cyclohexane. Cyclohexane-1,2,3-triol includes three steric isomers, and any of them can be employed as starting material of this invention. Cyclohexane-1,2,3-triol can be supplied to the reaction system as vest state or as a solution in an appropriate solvent, such as water. Since the presence of water can prolong the catalyst life, the use of an aqueous solution is preferred.

Platinum metals which can be used in the catalyst system according to this invention include, for example, rethenium, rhodium, palladium, osmium, irridium and platinum. In view of their high selectivity of pyrogallol, the preferred metals are irridium, rhodium and palladium, in particular palladium.

The platinum group metal can be used alone as a catalyst component. However, in order to improve the selectivity of pyrogallol, such modifier can be used as (a) at least one member of alkali metal salts and/or (b) at least one member selected from the group consisting of indium, antimony, bismuth, selenium, tellurium, arsenic, copper, silver, gold and zinc.

Although the mechanism of the alkali metal salt of group (a) has not yet been fully clarified, it stabilizes the selectivity of pyrogallol and the salt prevents formation of catechol as a byproduct. Examples of the alkali metal salts include sulfates, carbonates, nitrates, bromides, chlorides and carboxylates such as acetates of sodium, potassium, rubidium, and cesium. Sodium and potassium salts are preferred, in particular sodium sulfate, potassium sulfate and potassium chloride. The incorporation of the modifier of group (b) also increases the selectivity of pyrogallol and stabilizes catalytic activity. Gold and tellurium are preferred modifier.

The carrier on which the catalyst system is supported is a porous solid having high surface area, such as, activated carbon, silica, alumina and silicon carbide. Porous carbon is preferred.

The deposition of the catalyst system on the carrier can be carried out by any of the conventional methods. Solutions of the platinum group metal compounds, the alkali metal salt and a compound of the group (b) modifier metal or a mixed solution thereof are prepared, then one or more solutions are applied to the carrier by immersion, adsorption, drying up or spraying and the compounds on the carrier are subjected to reduction treatment. Alternatively, the platinum group metal compound is deposited on the carrier and reduced, then the alkali metal salt and/or the group (b) modifier metal compound are deposited on the carrier and reduced, if necessary. The order of deposition of the platinum group metal compound, and the modifier (a) compound and/or the modifier (b) metal compound is not critical and therefore they may be deposited simultaneously or separately in any order.

The amount of the platinum group metal to be deposited on the carrier may vary depending upon the kind of the platinum group metal and, in general, ranges within 1 to 50 wt% of the carrier. The amount of the alkali metal salt deposited is not critical but, in general, an amount of 0.3 to 30 wt%, preferably 1 to 10 wt% based on the amount of the carrier is used. The amount of the group (b) modifier may also vary depending upon the kind of the metal and the kind of the platinum group metal, an appropriate proportion is within from 0.02 to 2 gram atoms preferably within from 0.05 to 0.5 gram atom per platinum group metal.

The platinum group metal compounds which may be used in the preparation of the catalyst are inorganic salts such as chlorides and nitrates and organic salts, for example, chloroplatinic acid, palladium chloride, rhodium trichloride, osmium tetrachloride, ruthenium trichloride, rhodium nitrate, palladium acetate and palladium nitrate.

Compounds of the group (b) modifier metal include, for example, chloroauric acid, silver acetate, silver nitrate, arsenic acid, selenic acid, telluric acid, tellurium dioxide, indium trichloride, antimony trichloride, bismuth trichloride, zinc chloride and cupric chloride.

Reduction of the platinum group metal compound and the group (b) modifier metal compound, if present, on the carrier may be effected by any of the conventional methods, for example, heating in a hydrogen stream. However, in order to increase the selectivity of pyrogallol, reduction is conveniently effected with methanol or by contacting with molecular hydrogen in an aqueous medium. In the case of methanol reduction, the metal compound(s) deposited on the carrier is contacted with methanol gas which is preferably diluted with an inert gas such as nitrogen, at a temperature within the range of from 100° to 500° C., preferably 200° to 400° C. In the case of hydrogen reduction, the carrier on which the metal compound(s) is deposited is dispersed in an aqueous medium to which molecular hydrogen is bubbled at a temperature of 0° to 100° C., usually room temperature, for several tens of minutes to several hours. After reduction treatment, the catalyst is preferably washed with water and dried.

After reduction, additional oxidation and reduction may be effected, or this cycle may be repeated a few times thereby further increasing the selectivity of pyrogallol. In this case, the oxidation is carried out in a gas stream containing molecular oxygen of 0.1 to 5 vol%, preferably 0.5 to 2 vol% at a temperature of 100° to 400° C., preferably 150° to 350° C.

The conversion rate of cyclohexane-1,2,3-triol of the process according to this invention may vary over a wide range depending upon the selection of reaction conditions, on the other hand, the selectivity of pyrogallol is dependent on the kind of catalyst employed as well as control of the reaction conditions, such as reaction temperature.

The preferred catalyst which gives higher selectivity of pyrogallol consists essentially of palladium as the platinum group metal and (a) sodium or potassium salt as the alkali metal salt and/or (b) tellurium or gold supported on activated carbon. After deposition, reduction is conveniently carried out with molecular hydrogen in an aqueous medium or with methanol and preferably then oxidation and reduction are repeated.

Dehydrogenation of cyclohexane-1,2,3-triol according to this invention is carried out in a stream of an inert gas which does not participate in the reaction, such as, nitrogen, argon, carbon dioxide, steam and methane at a temperature of 50° to 500° C., preferably 150° to 350° C., more preferably 250° to 300° C. and under atmospheric to a reduced pressure. The reaction can be carried out in either a liquid phase or a gas phase. In order to prevent dissolving out of an alkali metal salt which is one of catalyst components and facilitate the separation of catalyst from the reaction product, a gas phase reaction is preferably employed.

Apparatus suitable for carrying out the process according to this invention is a fixed bed flow reactor to which cyclohexane-1,2,3-triol is introduced at a rate, in terms of space velocity (SP), of 0.01 to 20 $hr^{-1}$, preferably 0.1 to 5 $hr^{-1}$. Cyclohexane-1,2,3-triol is often supplied in an aqueous solution. An inert gas is introduced at a gas hourly space velocity (GHSV) of 50 to 100,000 $hr^{-1}$ preferably 1,000 to 40,000 $hr^{-1}$ at N.T.P.

The presence of a hydrogen acceptor in the reaction system increases the selectivity of pyrogallol. Examples of the acceptor are unsaturated hydrocarbons, for example, ethylene, benzene, allylalcohol, diallyl ether, cyclohexene and acetylene. The amount of the acceptor is 0.1 to 50 moles, preferably 0.5 to 5 moles per cyclohexane-1,2,3-triol.

The reaction product contains pyrogallol, catechol byproduct and unreacted starting material, and pyrogallol can be separated and purified by, for example, distillation extraction and crystallization.

The physical properties of cyclohexane-1,2,3-triol are close to those of pyrogallol, the separation of them by distillation requires complicated operation conditions and is inpractical. It has been found that pyrogallol product can effectively be extracted from a mixture of cyclohexane-1,2,3-triol therewith by an appropriate solvent. The solvens are alcohols, ethers, acetals, ketones, acid anhydrides, esters, nitriles and nitroalkanes. The alcohols include, for example, alkanols, such as, methanol, ethanol, i-propyl alcohol, n-, i- or t-butyl alcohol and 2-ethylhexanol, and aralkyl alcohols, such as, benzyl alcohol and furfuryl alcohol. The ethers include, for example, aliphatic ethers, such as diethyl ether, di-i-propyl ether and ethylene glycol monomethyl ether, and cyclic ethers, such as, tetrahydrofuran, 1,4-dioxane and cyclohexane oxide. The acetals are those derived from a ketone and an aldehyde and include, for example, acetaldehyde diethylacetal and cyclohexanone dimethylacetal. The ketones are, for example, acetone, methyl ethyl ketone, i-butyl methyl ketone, cyclohexanone and acetophenone. Examples of the acid anhydride are aliphatic acid anhydrides, such as, acetic anhydride and propionic anhydride. The esters are alkyl esters of aliphatic and aromatic acid, such as, methyl acetate, ethyl acetate, butyl acetate, i-propyl formate, ethylene glycol monoacetate and methyl benzoate. Acetonitrile, acrylonitrile and benzonitrile are examples of the nitriles. An example of nitroalkane is nitromethane.

The amount of the solvent to be used is usually 0.2 to 10 times, by weight, that of the pyrogallol and the optimum amount may vary depending upon the amount of impurities in the reaction product and the type of solvent employed. For example, acetone is the solvent then the amount is conveniently 0.5 to 2 times by weight that of the pyrogallol. The temperature at which extraction is effected is not critical so long as the solvent is maintained as a liquid. In general, for the extraction, a solvent which is a liquid at room temperature is used at a temperature of room temperature to about 80° C.

Since pyrogallol is highly reactive with oxygen, it is preferred that the extraction be carried out in a stream of an inert gas, such as nitrogen.

With the extraction, pyrogallol is transferred into the solvent and cyclohexane-1,2,3-triol is left undissolved. When pyrogallol and the triol are dissolved in an aqueous medium, the pyrogallol can be separated by means of a liquid-liquid extraction using a water-immiscible solvent selected from an ether, a ketone and an ester. The solvent is removed from the extract by, for example, distillation and the residue is purified in any conventional way, for example, by recrystallization to obtain the desired product of pyrogallol having high purity.

When a water-miscible solvent, such as, an alcohol and a ketone is used, it is necessary to remove water from the mixture of pyrogallol and the triol as completely as possible before use.

The catalyst which has been used and deactivated can be regenerated by appropriate regeneration treatment.

The catalyst preferred for use in this invention is a palladium catalyst supported on activated carbon. In this case, however, the conventional regeneration treatment of a noble metal catalyst including calcining the catalyst at 400° to 600° C. under molecular oxygen-containing gas atmosphere to burn off the deposit on the catalyst and oxidizing the metal followed by reducing the noble metal oxide into its corresponding elemental metal can not be applied, because the calcination step results in combustion of the carrier.

It has been found that regeneration of a deactivated palladium catalyst supported on activated carbon can conveniently be carried out by treating the used catalyst at a temperature of 220° to 400° C., preferably 250° to 350° C. under a low concentration molecular oxygen-containing gas atmosphere to restore the catalyst activity. In this case, to complete the regeneration procedures with reduction treatment following oxidation does not improved the activity and stability of the regenerated catalyst. The oxidation atmosphere is an inert gas such as nitrogen, argon, carbon dioxide and steam containing 0.1 to 10 vol%, preferably 0.5 to 3 vol% of oxygen. As the oxidation temperature is lowered, the oxygen concentration may be increased. The oxidation time may vary depending upon the temperature, oxygen concentration and the flow rate if the oxygen-containing gas is flowed and ranges usually from 10 minutes to about 20 hours.

When, the oxidation treatment has been completed, the regenerated catalyst is ready for use in further dehydrogenation, therefore, if the catalytic activity drops, the feed of the starting material is stopped and a molecular oxygen-containing gas is directly passed through the catalyst bed to restore the activity without requiring separate operation.

Alternatively, regeneration of the catalyst can be made with steam, that is, steam is passed through the catalyst bed at a temperature of 300° to 600° C., preferably 350° to 450° C. at an LHSV, in terms of water, of 0.1 to 100 hr$^{-1}$, for 0.1 to 10 hours preferably 0.5 to 5 hours. This treatment is advantageous in that there is less combustion of activated carbon carrier.

One feature of the process according to this invention is that the production of pyrogallol by dehydrogenation of cyclohexane-1,2,3-triol in the presence of a platinum group metal catalyst is effected in an inert gas stream thereby sharply increasing the selectivity of pyrogallol. This is unique and is distinguished from the production of catechol by dehydrogenation of cyclohexane-1,2-diol which process does not alter the selectivity of catechol, as the reaction is carried out in either an inert gas stream or a hydrogen stream.

The process according to this invention makes it possible to produce pyrogallol from a low cost starting material which is readily available. The starting material is cyclohexane-1,2,3-triol which is obtained, for example, by hydration of an oxidation product of cyclohexane.

This invention will be illustrated in detail by the following examples. However, it should be understood that this invention is in no way limited to these examples. In the examples, percentage of catalyst components is by weight based on that of the carrier, unless otherwise specifically defined.

EXAMPLE 1

Preparation of catalyst 2.5 Grams of palladium chloride was dissolved in 6 ml of concentrated hydrochloric acid and the mixture was diluted with water to make 15 ml of an aqueous solution in which 5 g of coconut shell activated carbon was immersed under a reduced pressure for a night. The activated carbon thus treated was dried by evaporating water from the mixture at 70° C. to dryness and packed into a glass calcining tube through which a nitrogen stream was passed at 100° C. for one hour and a hydrogen stream at 400° C. for 3 hours to effect reduction of palladium chloride to obtain a catalyst. This catalyst was used in Runs Nos. 1, 2 and 4.

The coconut shell activated carbon treated with palladium chloride as above was immersed in 12.5 ml of a 1% aqueous potassium sulfate solution for one hour, dried and subjected to reduction treatment as above to obtain a palladium/activated carbon catalyst containing 2.5 wt% of potassium sulfate. This catalyst was used in Run No. 4.

DEHYDROGENATION 0.5 Milliliter of each of the catalysts was packed in a glass tube and heated at 300° C., then nitrogen, carbon dioxide or hydrogen was passed through the tube at a GHSV of 5,000 hr$^{-1}$ while a 10% aqueous solution of cyclohexane 1,2,3-triol (melting point 110°–120° C., recrystallized from ethyl acetate) was supplied to the tube at an LHSV of 2.7 hr$^{-1}$ to conduct continuous dehydrogenation under atmoshperic pressure. The discharged reaction mixture was cooled with ice-water, and gas and liquid phases were separated. The product was subjected to gas chromatography. The conversion of cyclohexane-1,2,3-triol and the selectivities of pyrogallol and catechol are given in Table 1.

TABLE 1

| Run No. | Catalyst | Gas | Conversion (%) | Selectivity (%) Pyrogallol | Catechol |
|---|---|---|---|---|---|
| 1 | Pd/C | $N_2$ | 23.0 | 42.2 | 30.6 |
| 2 | Pd/C | $CO_2$ | 12.1 | 42.0 | 34.0 |
| 3 | Pd—$K_2SO_4$/C | $N_2$ | 51.1 | 59.2 | 29.1 |
| 4* | Pd/C | $H_2$ | 82.8 | 7.7 | 76.7 |

Note:
*Run 4 was for comparison.

COMPARATIVE EXAMPLE 1

An activated carbon supported catalyst containing 1.5 wt% of palladium and 4 wt% of potassium carbonate was prepared according to procedures similar to those of Example 1.

Dehydrogenation was carried out according to procedures similar to those of Example 1 excepting that hydrogen and a 10 wt% aqueous cyclohexane-1,2,3-triol solution were passed through at a GHSV of 5,000 hr$^{-1}$ and at an LHSV of 2.2 hr$^{-1}$, respectively. The conversion of cyclohexane-1,2,3-triol was 100% and the selectivity of pyrogallol was 4.8%, the main product being catechol.

COMPARATIVE EXAMPLE 2

Procedures similar to those of Example 1 using nitrogen were repeated excepting that, instead of cyclohexane-1,2,3-triol, a 10 wt% aqueous trans cyclohexane-1,2-diol solution was employed. The conversion of the diol was 94.2% and the selectivity of catechol was 81.7%. Then, nitrogen was changed to hydrogen, the conversion and the selectivity were 87.1% and 82.4%. Thus, no significant difference between both atmosphere was observed.

EXAMPLE 2

Three kinds of palladium/activated carbon catalysts containing 2.0 wt% of potassium carbonate, 2.0 wt% of sodium sulfate and 4.0 wt% of cesium chloride, respectively, were prepared according to procedures similar to those of Example 1. Dehydrogenation was carried out using nitrogen gas under conditions given in Example 1. The conversion of cyclohexane-1,2,3-triol and the selectivity of pyrogallol are given in Table 2.

TABLE 2

| Run No. | Catalyst | Conversion (%) | Selectivity (%) |
|---|---|---|---|
| 5 | Pd—$K_2CO_3$/C | 23.3 | 49.3 |
| 6 | Pd—$Na_2SO_4$/C | 10.9 | 45.3 |
| 7 | Pd—CsCl/C | 18.9 | 49.1 |

EXAMPLE 3

In this Example, preparation of catalysts and dehydrogenation using nitrogen were carried out as in Example 1.

Platinum/activated carbon catalyst from chloroplatinic acid, rhodium/activated carbon catalyst from rhodium trichloride, osmium/activated carbon catalyst from osmium tetrachloride and ruthenium/activated carbon catalyst from ruthenium trichloride were prepared.

The conversion of cyclohexane-1,2,3-triol and the selectivity of pyrogallol are given in Table 3.

TABLE 3

| Run No. | Catalyst | Conversion (%) | Selectivity (%) |
|---|---|---|---|
| 8 | Pt/C | 35.4 | 23.4 |
| 9 | Rh/C | 48.0 | 39.3 |
| 10 | Os/C | 11.5 | 30.0 |
| 11 | Ru/C | 49.0 | 17.0 |

EXAMPLE 4

Using 5 wt% iridium/activated carbon catalyst available from Nippon Engelhard Co., Ltd., Tokyo, Japan and 5 wt% iridium-2 wt% potassium carbonate/activated carbon catalyst, cyclohexane-1,2,3-triol was dehydrogenated as in Example 1 with nitrogen stream but the reaction temperature being 350° C. and the LHSV of 10 wt% aqueous cyclohexane-1,2,3-triol solution being 5.5 hr$^{-1}$.

The conversion of the triol and the selectivity of pyrogallol are given in Table 4.

TABLE 4

| Run No. | Catalyst | Conversion (%) | Selectivity (%) |
|---|---|---|---|
| 12 | Ir/C | 6.6 | 22.7 |
| 13 | Ir/$K_2CO_3$/C | 14.0 | 32.4 |

EXAMPLE 5

Preparation of Pd-Au-$K_2SO_4$/C catalyst 2.5 Grams of palladium chloride was dissolved in 6 ml of concentrated hydrochloric acid to which 0.931 g of chloroauric acid and water were added to make 15 ml of an aqueous solution. 5 Grams of coconut shell activated carbon was immersed in the solution under a reduced pressure for a night and dried at 70° C. to dryness. The activated carbon thus treated was immersed in a 10% aqueous potassium sulfate solution for one hour, dried, heated at 100° C. for one hour in a nitrogen stream and subjected to reduction at 400° C. for 3 hours in a hydrogen stream to obtain a Pd-Au-$K_2SO_4$(2.5 wt%)/C catalyst.

Preparation of Pd-Ag-$K_2SO_4$/C catalyst 2.5 Grams of palladium chloride was dissolved in 6 ml of concentrated hydrochloric acid to which water was added to obtain 15 ml of an aqueous solution. Five grams of coconut shell activated carbon was immersed in the solution under a reduced pressure for a night, dried at 70° C., heated at 150° C. for one hour in a nitrogen stream and the palladium chloride was reduced at 400° C. for 3 hours in a hydrogen stream. The activated carbon thus treated was immersed in 15 ml of an aqueous solution containing 0.243 g of silver nitrate and dried, then as in Example 1, 2.5 wt% of potassium sulfate was supported on the activated carbon which was then subjected to reduction treatment at 500° C. for 3 hours in a hydrogen stream to obtain a catalyst.

Preparation of Pd-As-$K_2SO_4$/C Catalyst

Activated carbon particles were treated with 15 ml of an aqueous solution containing 2.5 g of palladium chloride, 6 ml of concentrated hydrochloric acid and 0.310 g of arsenic acid. Then, procedures as in the preparation of Pd-Au-$K_2SO_4$/C catalyst were repeated to give a Pd-As-$K_2SO_4$/C catalyst.

Preparation of Pd-Se-$K_2SO_4$/C Catalyst

Procedures similar to those of preparation of Pd-As-$K_2SO_4$/C catalyst were repeated using 0.819 g of selenic acid (a 40 wt% aqueous solution) instead of arsenic acid to give a Pd-Se-$K_2SO_4$/C catalyst.

With these catalyst, dehydrogenation of cyclohexane-1,2,3-triol was catalyzed in a nitrogen stream under the conditions of Example 1.

The conversion of the triol and the selectivity of pyrogallol are given in Table 5.

TABLE 5

| Run No. | Catalyst | Conversion (%) | Selectivity (%) |
|---|---|---|---|
| 14 | Pd—Au—$K_2SO_4$/C | 86.8 | 71.4 |
| 15 | Pd—Ag—$K_2SO_4$/C | 15.2 | 67.2 |
| 16 | Pd—As—$K_2SO_4$/C | 83.4 | 68.2 |
| 17 | Pd—Se—$K_2SO_4$/C | 48.8 | 62.8 |

EXAMPLE 6

Catalysts supported on activated carbon and having the following compositions were prepared as in Example 1 using a solution of palladium chloride in dilute hydrochloric acid, an aqueous telluric acid solution and an aqueous potassium sulfate solution.

One milliliter each of these catalysts was packed in a reaction tube and heated at 300° C. Nitrogen and a 10 wt% aqueous cyclohexane-1,2,3-triol solution were introduced to the reaction tube.

The reaction conditions and the conversion of the triol and selectivity of pyrogallol are given in Table 6.

TABLE 6

| Run No. | Catalyst Components | | | GHSV (hr$^{-1}$) | LHSV (hr$^{-1}$) | Conversion (%) | Selectivity (%) |
|---|---|---|---|---|---|---|---|
| | Pd (wt %) | Te (wt %) | K$_2$SO$_4$ (wt %) | | | | |
| 18 | 30 | 5.8 | 2.5 | 2900 | 2.5 | 99.3 | 55.9 |
| 19 | 30 | 5.8 | — | 9000 | 55 | 56.3 | 38.0 |

EXAMPLE 7

Two catalysts were prepared by suspending 5 g of activated carbon supported palladium chloride. Modification was made by adding chloroauric acid or telluric acid in the amounts of 10 wt%, in terms of palladium, and 0.16 gram atom of Au or Te per Pd in 50 ml of water and bubbling hydrogen into the mixture at room temperature for 3 hours to effect reduction. After filtration, the carbon was washed with water until washings became neutral and dried at 60° C. in vacuo. Then, the carbon was immersed in an aqueous solution containing 0.197 g of potassium sulfate and dried by evaporation to obtain a catalyst containing 2.5 wt% of potassium sulfate. 0.4 Milliliter each of the catalysts so prepared was packed in a reaction tube and heated at 300° C., then nitrogen and a 10 wt% aqueous cyclohexane-1,2,3-triol were supplied to the tube at a GHSV of 9,000 hr$^{-1}$ and an LHSV of 27 hr$^{-1}$, respectively.

The conversion of the triol and the selectivity of pyrogallol after 6 hours from the reaction started are given in Table 7.

TABLE 7

| Run No. | Catalyst | Amount of H$_2$ (l/hr) | Conversion (%) | Selectivity (%) |
|---|---|---|---|---|
| 20 | Pd—Au—K$_2$SO$_4$/C | 12.9 | 15.8 | 79.6 |
| 21 | Pd—Te—K$_2$SO$_4$/C | 10.0 | 17.9 | 77.7 |

EXAMPLE 8

Following procedures similar to those of Example 6, a Pd-Te-K$_2$SO$_4$/C catalyst (Pd: 30 wt%, Te/Pd: 0.16, K$_2$SO$_4$: 2.5 wt%) was prepared. 0.5 Milliliter of the catalyst was packed in a glass tube and heated at 280° C., then nitrogen and a 10 wt% aqueous cyclohexane-1,2,3-triol solution were introduced to the tube at a GHSV of 5,000 hr$^{-1}$ and an LHSV of 55 hr$^{-1}$, respectively to effect reduction of the triol for 2 hours.

The conversion of the triol and the selectivity of pyrogallol at 1 hour and 2 hours after the reaction started are given in Table 8.

The catalyst used in the above reaction was regenerated by introducing nitrogen containing 2 vol% of oxygen at 250° C., at a GHSV of 6,000 hr$^{-1}$ for 1.5 hours. After purging the catalyst with nitrogen, dehydrogenation of the triol was carried out again under the conditions above. Regenerations were also effected at various temperatures.

The conversion and the selectivity using the regenerated catalyst are also given in Table 8.

TABLE 8

| Run No. | Catalyst | Temp. (°C.) | Conversion (%) | | Selectivity (%) |
|---|---|---|---|---|---|
| | | | 1 hr. | 2 hrs. | |
| 22 | Fresh | | 22.3 | 4.9 | 44.9 |
| | Regenerated | 250 | 29.1 | 15.7 | 45.9 |
| 23 | Regenerated | 220 | 11.1 | — | 40.8 |
| 24 | " | 300 | 30.3 | — | 44.9 |
| 25 | " | 200 | 2.1 | — | 41.4 |

TABLE 8-continued

| Run No. | Catalyst | Temp. (°C.) | Conversion (%) | | Selectivity (%) |
|---|---|---|---|---|---|
| | | | 1 hr. | 2 hrs. | |
| 26* | " | 250 | 12.9 | 3.7 | 42.4 |

Note:
*After regeneration, further reduction at 400° C. for 3 hours in H$_2$ stream.

EXAMPLE 9

Three grams of coconut shell activated carbon was immersed in an aqueous solution containing 0.311 g of palladium chloride, 0.058 g of telluric acid and 0.45 ml of concentrated hydrochloric acid at room temperature, for one hour. The carbon was filtered in vacuo, dried at 60° C. in vacuo for 30 minutes and immersed in an aqueous solution containing 0.087 g of potassium sulfate, then the mixture was dried by evaporation of water. The carbon thus treated was dried at 150° C. for one hour in a nitrogen stream and packed in a glass tube to which nitrogen containing 8 vol% of methanol was passed through at a GHSV of 1,000 hr$^{-1}$, at 200° C. for 2 hours and at 400° C. for 2 hours to prepare a catalyst (Run No. 27).

Instead of methanol-containing nitrogen, hydrogen was passed through the tube at 400° C. for 3 hours to obtain another catalyst (Run No. 28).

0.4 Milliliter of the catalyst was packed in a reaction tube and heated at 300° C., then nitrogen and a 10 wt% aqueous cyclohexane-1,2,3-triol solution were introduced to the tube at a GHSV of 9,000 hr$^{-1}$ and an LHSV of 27 hr$^{-1}$, respectively, to carry out dehydrogenation for 2 hours.

The deactivated catalyst was regenerated by introducing nitrogen containing 2 vol% of oxygen at 300° C. and a GHSV of 6,000 hr$^{-1}$ for one hour. Then, dehydrogenation of the triol was carried out again under the conditions above for 2 hours.

The conversion of the triol and the selectivity of pyrogallol are given in Table 9.

TABLE 9

| Run No. | Catalyst | Reaction time (hr) | Conversion (%) | Selectivity (%) |
|---|---|---|---|---|
| 27 | Fresh | 1 | 20.1 | 71.8 |
| | | 2 | 13.3 | 70.0 |
| | Regenerated | 1 | 28.4 | 67.3 |
| | | 2 | 17.8 | 70.2 |
| 28 | Fresh | 1 | 39.1 | 54.3 |
| | | 2 | 27.8 | 60.0 |
| | Regenerated | 1 | 43.1 | 58.5 |
| | | 2 | 27.0 | 59.7 |

EXAMPLE 10

Procedures similar to those of Example 1 were repeated but various compounds listed in Table 10 were added to the aqueous palladium chloride solution to prepare catalysts containing pottasium sulfate.

TABLE 10

| Run No. | Additive | | Catalyst |
|---|---|---|---|
| 29 | HAuCl$_4$ | 0.931 g | Pd—Au—K$_2$SO$_4$ |
| 30 | InCl$_3$ | 0.50 g | Pd—In—K$_2$SO$_4$ |
| 31 | SbCl$_3$ | 0.50 g | Pd—Sb—K$_2$SO$_4$ |
| 32 | BiCl$_3$ | 0.71 g | Pd—Bi—K$_2$SO$_4$ |
| 33 | 40 wt % aq. H$_2$SeO$_4$ | 0.819 g | Pd—Se—K$_2$SO$_4$ |
| 34 | CuCl$_2$ | 0.39 g | Pd—Cu—K$_2$SO$_4$ |
| 35 | ZnCl$_2$ | 0.308 g | Pd—Zn—K$_2$SO$_4$ |

TABLE 10-continued

| Run No. | Additive | Catalyst | |
|---|---|---|---|
| 36 | AgNO$_3$ | 0.243 g | Pd—Ag—K$_2$SO$_4$ |

Using 0.5 ml of these catalyst, dehydrogenation of cyclohexane-1,2,3-triol was carried out for 2 hours under conditions mentioned below.

| | |
|---|---|
| Temperature | 300° C. |
| GHSV of nitrogen | 5,000 hr$^{-1}$ |
| LHSV of 10% aqueous triol solution | 27 hr$^{-1}$ |

Then, deactivated catalyst was regenerated with nitrogen containing 2 vol% of oxygen at 250° C. for one hour. The regenerated catalyst was used again for dehydrogenation.

Results obtained are given in Table 11.

TABLE 11

| Cat. No. | Cat. | Conversion (%) 1 hr. | Conversion (%) 2 hrs. | Selectivity (%) 1 hr. | Selectivity (%) 2 hrs. |
|---|---|---|---|---|---|
| 29 | A | 86.8 | 60.8 | 71.4 | |
| | B | 92.8 | 70.6 | 71.4 | |
| 30 | A | 99.4 | 69.7 | 45.3 | 52.3 |
| | B | 99.2 | | 42.1 | |
| 31 | A | 99.5 | 91.3 | 53.0 | 56.2 |
| | B | 98.1 | | 49.8 | |
| 32 | A | 79.0 | 44.1 | 44.2 | 32.0 |
| | B | 79.1 | | 41.2 | |
| 33 | A | 48.8 | 15.7 | 62.8 | 65.4 |
| | B | 63.7 | | 62.8 | |
| 34 | A | 67.1 | 39.0 | 60.1 | 62.3 |
| | B | 67.8 | | 57.9 | |
| 35 | A | 67.8 | 31.0 | 54.3 | 52.2 |
| | B | 67.9 | | 48.7 | |
| 36 | A | 15.2 | 6.0 | 67.2 | 64.9 |
| | B | 18.0 | | 62.9 | |

Note:
A: Freshly prepared.
B: Regenerated.

EXAMPLE 11

Preparation of catalyst

Thirty grams of coconut shell activated carbon was immersed in 90 ml of an aqueous solution containing 3.11 g of palladium chloride, 0.58 g of telluric acid and 4.5 ml of concentrated hydrochloric acid for one hour, filtered in vacuo and dried at 60° C. under a pressure of 30 mmHg for 30 minutes. Then, the carbon was immersed in 90 ml of an aqueous solution containing 0.87 g of pottasium sulfate and dried at 60° C. in vacuo. The carbon thus treated was packed in a tube and activated according to reduction and oxidation treatment schedule mentioned below.

| | Flow rate: GHSV of 1,300 hr$^{-1}$ | | |
|---|---|---|---|
| Step | Gas | Temp. (°C.) | Time (hr) |
| 1st reduction | N$_2$ | 150 | 1 |
| | H$_2$ | 200 | 1 |
| | H$_2$ | 400 | 2 |
| 1st oxidation | N$_2$ | 200 | 1 |
| | N$_2$ + 2% O$_2$ | 270–300 | 8 |
| 2nd reduction | N$_2$ | 150 | 1 |
| | H$_2$ | 200 | 1 |
| | H$_2$ | 400 | 2 |
| 2nd oxidation | N$_2$ | 200 | 1 |
| | N$_2$ + 2% O$_2$ | 250–300 | 2 |
| 3rd reduction | N$_2$ | 150 | 1 |
| | H$_2$ | 200 | 1 |
| | H$_2$ | 400 | 2 |

Dehydrogenation 0.4 Milliliter of the catalyst was packed in a reaction tube to which nitrogen and a 10 wt% of aqueous cyclohexane-1,2,3-triol solution were introduced at a GHSV of 9,000 hr$^{-1}$ and an LHSV of 27 hr$^{-1}$, respectively, to conduct dehydrogenation at 300° C.

After two hours, the catalytic activity lowered, so introduction of nitrogen and the solution was stopped and nitrogen containing 2% oxygen was introduced at 270° C. and a GHSV of 6,000 hr$^{-1}$ for one hour to effect regeneration.

The results are given in Table 12.

TABLE 12

| Run No. | Catalyst | Reaction time (hr) | Conversion (%) | Selectivity (%) |
|---|---|---|---|---|
| 37 | Freshly prepared | 1 | 48.2 | 70.9 |
| | | 2 | 31.4 | 71.9 |
| 38 | Regenerated | 1 | 45.5 | 68.1 |
| | | 2 | 31.3 | 69.6 |

EXAMPLE 12

Under nitrogen atmosphere, a mixture of pyrogallol and cyclohexane-1,2,3-triol and solvents given in Table 13 were agitated at 25° C. for 15 minutes, then, the solvent was separated. The amounts of pyrogallol and the triol dissolved in the solvent were determined and an extraction selectivity($\alpha$) was calculated according to following equation:

$$\alpha = \frac{\text{Solubility of Pyrogallol} - \text{Solubility of Triol}}{\text{Solubility of Pyrogallol} + \text{Solubility of Triol}} \times 100$$

wherein the $\alpha$ was expressed in % and the solubility was expressed in g/ml.

The results are also given in Table 13.

TABLE 13

| Run No. | Solvent Kind | Solvent Amount (ml) | Pyrogallol (g) | Dicyclohexane-1,2,3-triol (g) | $\alpha$ (%) |
|---|---|---|---|---|---|
| 39 | Methanol | 5 | 5.165 | 1.307 | 60.4 |
| 40 | i-Propanol | 5 | 2.775 | 0.188 | 85.7 |
| 41 | n-Butanol | 5 | 5.210 | 0.317 | 81.4 |
| 42 | 2-Ethylhexanol | 5 | 2.390 | 0.257 | 70.6 |
| 43 | Furfuryl alcohol | 5 | 2.630 | 0.363 | 66.8 |
| 44 | Ethyleneglycol monomethyl ether | 5 | 3.330 | 1.101 | 63.0 |
| 45 | Di-i-propyl ether | 5 | 3.545 | 0.299 | 98.6 |
| 46 | 1,4-Dioxane | 2 | 1.176 | 0.314 | 91.2 |
| 47 | Tetrahydrofuran | 5 | 4.415 | 0.379 | 94.6 |

TABLE 13-continued

| Run No. | Solvent Kind | Amount (ml) | Pyrogallol (g) | Dicyclohexane-1,2,3-triol (g) | α (%) |
|---|---|---|---|---|---|
| 48 | Cyclohexeneoxide | 5 | 3.285 | 0.343 | 95.2 |
| 49 | Acetoaldehyde diethylacetal | 5 | 3.410 | 0.366 | 98.3 |
| 50 | Acetone | 1 | 1.101 | 0.121 | 99.1 |
| 51 | Ethyl methyl ketone | 5 | 5.695 | 0.530 | 98.4 |
| 52 | i-Butyl methyl ketone | 3 | 1.551 | 0.297 | 97.4 |
| 53 | Cyclohexanone | 5 | 2.770 | 0.475 | 99.3 |
| 54 | Acetic anhydride | 5 | 2.850 | 0.984 | 93.0 |
| 55 | Methyl acetate | 5 | 4.130 | 0.287 | 97.3 |
| 56 | Ethyl acetate | 5 | 2.473 | 0.975 | 98.4 |
| 57 | Butyl acetate | 5 | 5.270 | 0.310 | 97.0 |
| 58 | Acetonitrile | 2 | 1.400 | 0.369 | 97.3 |
| 59 | Nitro methane | 5 | 2.815 | 0.342 | 85.3 |
| 60* | Acetic acid | 5 | 2.645 | 1.193 | 7.8 |
| 61* | Dimethyl sulfoxide | 5 | 3.453 | 3.283 | −7.9 |

Note:
*For comparison.

EXAMPLE 13

Nitrogen and an aqueous cyclohexane-1,2,3-triol solution were introduced into a catalyst of palladium and potassium sulfate supported on activated carbon at 300° C. under atmospheric pressure to effect dehydrogenation. 120 Milliliters of the reaction product was mixed with 240 ml of i-butyl methyl ketone and extraction was carried out as in Example 12.

The compositions of the reaction product, the extract and the raffinate are given in Table 14.

TABLE 14

| Component | Amount (g) in reaction product | in extract | in raffinate |
|---|---|---|---|
| Pyrogallol | 4.76 | 4.16 | 0.60 |
| Catechol | 1.98 | 1.96 | 0.02 |
| Phenol | 0.08 | 0.07 | 0.01 |
| Cyclohexane-1,2,3-triol | 1.98 | 0.19 | 1.79 |
| Cyclohexane-1,2-diol | 0.02 | 0.01 | 0.01 |

EXAMPLE 14

0.4 Milliliter of a catalyst containing 3.6% Pd-0.8% Te-0.7% $K_2SO_4$/C was packed in a reaction tube to which nitrogen at a GHSV of 9,000 hr$^{-1}$ and a 10% aqueous cyclohexane-1,2,3-triol solution at an LHSV of 27 hr$^{-1}$ were introduced and dehydrogenation was carried out at 300° C. After one hour from the reaction started, the conversion of the triol was 18.4% and the selectivity of pyrogallol was 61.7%.

When the reaction was continued for further 4 hours, the conversion lowered to 7.4%. Then, supply of the aqueous solution was stopped, and water and nitrogen were introduced at an LHSV of 27 hr$^{-1}$ and at a GHSV of 2,000 hr$^{-1}$, respectively, and regeneration was carried out at 400° C. for 3 hours.

Dehydrogenation was restarted under the same conditions above and, after one hour, the conversion and the selectivity were found to be 19.8% and 61.7%.

EXAMPLE 15

One milliliter of the catalyst prepared in Example 14 was packed in a reaction tube. Dehydrogenation was carried out by supplying to the tube heated at 260° C. a 5% aqueous cyclohexane-1,2,3-triol at an LHSV of 3.4 hr$^{-1}$ and nitrogen stream of atmospheric pressure at a GHSV of 3,000 hr$^{-1}$.

The catalyst activity was maintained for a long time without change. Little or no deactivation was observed after 8 hours from the reaction started, the conversion of the triol being 44.2%, the selectivity of pyrogallol being 56.4% and the selectivity of catechol being 36.8%.

What is claimed is:

1. A process for producing pyrogallol comprising subjecting cyclohexane-1,2,3-triol to dehydrogenation in the presence of a platinum group metal catalyst in an inert gas stream.

2. A process for producing pyrogallol in accordance with claim 1, wherein there is used, as a modifier, an alkali metal salt.

3. A process for producing pyrogallol in accordance with claim 1 or 2, wherein said platinum group metal is palladium.

4. A process for producing pyrogallol in accordance with claim 3, wherein there is used, as a modifier, at least one member selected from the group consisting of gold, tellurium, silver, arsenic, selenium, indium, antimony, bismuth, copper and zinc.

5. A process for producing pyrogallol in accordance with claims 1, 2, 3 or 4, wherein said catalyst is supported on a carrier.

6. A process for producing pyrogallol in accordance with claim 5, wherein said carrier is activated carbon.

7. A process for producing pyrogallol in accordance with claim 4, wherein said modifier is gold.

8. A process for producing pyrogallol in accordance with claim 4, wherein said modifier is tellurium.

9. A process for producing pyrogallol in accordance with claim 5, wherein the amount of said platinum group metal is 1 to 50% by weight based on said carrier.

10. A process for producing pyrogallol in accordance with claim 5, wherein the amount of said alkali metal salt is 0.3 to 30% by weight based on said carrier.

11. A process for producing pyrogallol in accordance with claim 4, wherein the amount of said modifier is 0.02 to 2 gram atoms per palladium.

12. A process for producing pyrogallol in accordance with claim 1, wherein said inert gas stream is at least one member selected from the group consisting of nitrogen, steam, carbon dioxide and methane.

13. A process for producing pyrogallol in accordance with claim 12, the gas hourly space velocity of said inert gas stream is 50 to 100,000 hr$^{-1}$ at N.P.T.

14. A process for producing pyrogallol in accordance with claim 1, wherein the space velocity of said cyclohexane-1,2,3-triol is 0.01 to 20 hr$^{-1}$.

15. A process for producing pyrogallol in accordance with claim 1, wherein said dehydrogenation is carried out at a temperature of 50° to 500° C.

16. A process for producing pyrogallol comprising introducing cyclohexane-1,2,3-triol and nitrogen and/or steam at a space velocity of 0.1 to 5 hr$^{-1}$ and a gas hourly space velocity of 1,000 to 40,000 hr$^{-1}$ at N.T.P., respectively, into a reactor packed with an activated carbon supported catalyst consisting essentially of palladium of 1 to 50% by weight based on the activated carbon, an alkali metal sulfate of 1 to 10% by weight based on the activated carbon and gold and/or tellurium of 0.05 to 0.5 gram atom per palladium and carrying out dehydrogenation of cyclohexane-1,2,3-triol at a temperature of 150° to 350° C.

17. A process for producing pyrogallol in accordance with claims 7 or 8, wherein said catalyst is prepared by subjecting a palladium compound, a compound of gold or tellurium and an alkali metal salt supported on activated carbon to reduction in an aqueous medium with molecular hydrogen.

18. A process for producing pyrogallol in accordance with claims 7 and 8, wherein said catalyst is prepared by subjecting a palladium compound, a compound of gold or tellurium and an alkali metal salt supported on activated carbon to reduction with methanol.

19. A process for producing pyrogallol in accordance with claim 14, wherein said cyclohexane-1,2,3-triol is supplied to the reaction system as an aqueous solution.

20. A process for producing pyrogallol in accordance with claim 19, wherein pyrogallol is separated from the aqueous reaction mixture by means of liquid-liquid extraction using a water-immiscible solvent selected from an ether, a ketone and an ester.

* * * * *